(12) United States Patent
Medley et al.

(10) Patent No.: US 7,780,674 B2
(45) Date of Patent: Aug. 24, 2010

(54) ASR PRESSURISER

(76) Inventors: Vicky Medley, 33 The Dairy, Henlow, Stevenage (GB) SG16 6JD; Rick Kowalski, 1 Minister Park, Cottam, Preston (GB) PR4 0BY; Matt Chandler, 6 Shaftesbury Avenue, Penwortham, Preston (GB) PR1 0AY; Andrew Cobb, The Ashtead Hospital, The Warren, Ashtead, Surrey (GB) KT21 2SB ( * ) Notice: Subject to any disclaimer, the term of this patent is extended or adjusted under 35 U.S.C. 154(b) by 445 days.

(21) Appl. No.: 11/697,072

(22) Filed: Apr. 5, 2007

(65) Prior Publication Data
US 2007/0276399 A1 Nov. 29, 2007

(51) Int. Cl.
*A61B 17/56* (2006.01)
*A61B 17/74* (2006.01)
*A61F 2/34* (2006.01)
*A61F 2/36* (2006.01)

(52) U.S. Cl. .................. 606/92; 606/60; 606/86 R; 606/89; 606/91

(58) Field of Classification Search .................. 606/60, 606/62, 86 R, 89, 91, 92, 266, 267, 287, 297
See application file for complete search history.

(56) References Cited

U.S. PATENT DOCUMENTS

| 4,007,494 | A | * | 2/1977 | Sauer | 623/23.12 |
| 4,035,848 | A | * | 7/1977 | Wagner | 623/23.12 |
| 4,123,806 | A | | 11/1978 | Amstutz et al. | |
| 4,328,593 | A | * | 5/1982 | Sutter et al. | 623/23.42 |
| 4,593,685 | A | | 6/1986 | McKay | |
| 4,752,296 | A | * | 6/1988 | Buechel et al. | 623/23.14 |
| 5,480,448 | A | * | 1/1996 | Mikhail | 623/22.24 |
| 5,728,160 | A | | 3/1998 | Draenert | |
| 6,156,069 | A | * | 12/2000 | Amstutz | 623/22.11 |
| 2004/0193168 | A1 | | 9/2004 | Long et al. | |
| 2004/0193175 | A1 | | 9/2004 | Maroney et al. | |

FOREIGN PATENT DOCUMENTS

| EP | 1316297 A | 6/2003 |
| GB | 2297911 A | 8/1996 |

OTHER PUBLICATIONS

UK Search Report dated Feb. 24, 2005.

* cited by examiner

*Primary Examiner*—Thomas C Barrett
*Assistant Examiner*—Sameh Boles

(57) ABSTRACT

An instrument for controlling the distribution of bone cement on the surface of the head of a bone to prepare the bone to receive a re-surfacing prosthesis comprises a hollow shell which can be fitted on to the head of the bone to define a space around the head. The shell is rotationally symmetrical and has a spike like projection extending axially from the internal surface of the shell. At least one rib is located on the internal surface of the shell, extending from the spike like projection or from close to it, towards the open face of the shell, which contacts cement on the head of the bone in a sweeping action when the shell is rotated around its axis on the head of the bone.

24 Claims, 3 Drawing Sheets

ASR PRESSURISER

This invention relates to an instrument for controlling the distribution of bone cement on the surface of the head of a bone which provides the ball component of a ball and socket joint, to prepare the head of the bone to receive a re-surfacing prosthesis.

When ball and socket joints such as hip joints and shoulder joints are damaged, it is common to replace the entire joint with a joint prosthesis. In the case of a damaged hip joint, replacement involves resection of the proximal femur and implantation of the femoral component of an orthopaedic joint, which includes a stem part which can be received in the intramedullary canal, and a head part with a convex bearing surface. The patient's acetabulum is prepared to receive the acetabular component of the joint prosthesis, which provides a concave bearing surface to articulate with the bearing surface on the femoral component. Frequently, bone cement is used to affix the components of the prosthesis within their respective prepared bone cavities.

When the condition of the femoral bone tissue is generally good, it can be desirable to retain much of the proximal femur. Techniques have been developed in which the femoral head is fitted within a hollow resurfacing shell. The resurfacing shell has a convex outer surface which is highly polished which enables it to act against the hollow bearing surface of an acetabular component. Such techniques are referred to as Articular Surface Replacement techniques. They have the advantage that the quantity of bone which has to be removed from the head of the bone is only small. A tool which can be used to prepare the head in this way is disclosed in International patent application no. GB03/04303.

A bone cement can be used to ensure that an appropriate bond is formed between a resurfacing shell and the prepared head of a femur or other bone. Bone cements which are used in the techniques known in the art tend to have a relatively low viscosity. They are used in a technique in which a quantity of the cement is provided within the resurfacing shell which is then fitted on to the prepared head. Reception of the head within the shell causes the cement to be displaced. Alternatively, the bone cement is applied to the head of the bone prior to the fixation of the implant. These techniques use low viscosity bone cement so that the excess cement can be successfully extruded.

Low viscosity bone cement is used with the current techniques as the high degree of bone cement flow enables the bone cement to sufficiently penetrate the cancellous bone. Furthermore, the use of a low viscosity cement ensures that the cement can be displaced when the shell is fitted on to the head of the bone, so that the shell can be properly seated.

However, the use of low viscosity bone cement for fixing a re-surfacing implant has a number of disadvantages. The low viscosity cement has to be mixed and applied to the prepared head of a bone in a very short time period. The surgical team is therefore placed under pressure and the flexibility of the technique is limited. It has been found that low viscosity bone cement can take approximately 20 minutes to set after mixing. Low viscosity bone cement has the further disadvantage that once the cement has been applied to the head of the bone the implant must be carefully held in place until the bone cement has set. Furthermore, it has been found that the pressurisation of low viscosity cement is difficult to sustain and control. This lack of control therefore leads to inadequate fixation of the bone cement to the head of the bone.

The current cementing techniques cannot be used with high viscosity bone cement as the forces required to extrude the excess bone cement of high viscosity from the head of a bone are too large. This would therefore make it impossible for the current techniques to provide a uniform distribution of high viscosity bone cement on the surface of the head of the bone and therefore the correct seating of the implant would be impossible.

Current Articular Surface Replacement cementing techniques promote a high degree of penetration of the cement into the bone beneath the pole of the implant with a progressive reduction in the degree of penetration of the cement towards the periphery of the implant. This variation in the degree of the penetration of the cement into the bone at the head of the bone can lead to a number of problems. Firstly, if there is a high mass of bone cement in the region of the pole of the implant this may lead to an increased temperature in the bone cement during the setting period which may give rise to elevated bone necrosis in the region of the pole of the implant. Secondly, an excess of bone cement in the polar region of the head of the bone would prevent the re-surfacing prosthesis from being properly seated on the head of the bone when the re-surfacing prosthesis is fitted. Furthermore a lower degree of penetration of the cement into the bone at the periphery of the implant will result in a lower level of fixation of the implant and therefore a lower torsional stability of the implant. Finally, if there is a low degree of adhesion of the bone cement at the implant/bone interface then the peripheral region will also be open to ingress by foreign particles.

Commonly, a re-surfacing shell has a stem extending along the polar axis, which is received in a bore in the head of the bone along the polar axis of the head. It has been found that the current cementing techniques have the further disadvantage that when the re-surfacing implant is fitted the bone cement is drawn down with the stem of the implant during insertion. This displacement of the bone cement potentially leads to a more secure fixation of the stem of the implant than the implant itself This has an additional clinical disadvantage of stress shielding which could result in a subsequent loss of bone adjacent to the implant underside.

Current cementing techniques lead to the extrusion of a significant amount of excess cement that is then required to be removed from the adjacent femoral bone, soft tissues and potentially the implant surface prior to implantation. This therefore has the subsequent risks of scratching caused by the radiopaque agent in the bone cement.

The present invention provides an instrument in the form of a hollow shell, with at least one rib located on its internal surface which contacts cement on the head of the bone in a sweeping action when the shell is rotated around its axis on the head of the bone.

Accordingly, in one aspect, the invention provides an instrument for controlling the distribution of bone cement on the surface of the head of a bone to prepare the bone to receive a re-surfacing prosthesis, the instrument comprising a hollow shell which can be fitted on to the head of the bone to define a space around the head, the hollow shell being rotationally symmetrical and having a spike like projection extending axially from the internal surface of the shell, and at least one rib located on the internal surface of the shell, extending from the spike like projection or from close to it, towards the open face of the shell, which contacts cement on the head of the bone in a sweeping action when the shell is rotated around its axis on the head of the bone.

The instrument of the invention can enable the distribution of bone cement on the surface of a head of a bone to be controlled. For example, it can control the thickness of the layer of cement on the surface of the bone which faces generally along the axis of the relevant portion of the bone (which is the axis of the head, for example the femoral neck axis in the case of an instrument for use in preparing a femur to receive the femoral component of a hip joint prosthesis). Control of the thickness of the bone cement in this region can be important to ensure that a resurfacing prosthesis component is properly seated on the bone. It has been found that failure to control the thickness of a cement mantle in this region can lead to fractures in the neck region due to improper seating of the joint prosthesis component. The advantages that are available from the present invention in helping to address this problem are therefore significant.

The instrument of the invention can help to ensure that an adequate layer of bone cement is provided on the surfaces of the bone which face away from the axis of the bone. In particular, the contact between the rib on the internal surface of the shell and cement on the bone can help to force the cement into the porous structure of the bone, which can be desirable to achieve adequate fixation. The instrument can also help to control the thickness of the cement mantle on the surfaces of the bone which face away from the axis of the bone. This can help to provide secure fixation between the bone and the internal surfaces of a hollow prosthesis component, close to the open edge of the component, which can provide an important contribution to fixation of a prosthesis component on the bone so that twisting forces can be resisted.

In use, the instrument is fitted on to the head of the bone which has been pre-coated with a bone cement, especially with a bone cement whose viscosity is such that it does not tend to flow freely from the bone after application. The instrument is then rotated about the polar axis of the head of the bone, preferably in a single direction. The rib can contact bone cement on the head of the bone in a sweeping action as the instrument is rotated. Bone cement which is caught by the rib as it sweeps over the head of the bone tends to accumulate in the cavity within the shell adjacent to the rib, and to be swept over the surface of the bone head by the leading edge of the rib. The action of the rib on the cement as it is rotated can cause cement to be forced into the porous structure of cancellous bone, including those surfaces of the bone which face generally away from the relevant axis of the bone. The thickness of the mantle of cement which is provided on the surface of the bone, especially the surfaces of the bone which face generally away from the bone axis, is then controlled by the clearance between the rib and the surface of the bone.

The axis about which the instrument is rotated is defined by the spike like projection which extends axially from the internal surface of the shell. The bone is prepared with an axially extending cavity in which the spike can be located. The spike might be tapered inwardly along its length from the root where it is connected to the shell to its distal tip. Preferably, the cavity is sized so that the spike is a tight sliding fit. This can help to minimise any wobbling motion of the instrument as it is rotated. Preferably, the depth of the cavity is controlled relative to the length of the spike to define the axial gap between the surface of the bone and the internal surface of the shell, at and around the bone axis. This can be important to ensure that bone cement is displaced adequately from the region of the shell around the axis. The axis in which the cavity is formed can be determined using known instruments, for example as disclosed in U.S. Pat. No. 6,595,999.

During rotation of the instrument on the bone head, some bone cement might be displaced from within the shell, and accumulate on the bone around the open end of the shell. It will often be desirable to remove such cement.

When the cement has been distributed appropriately on the surface of the bone, the instrument is removed from the bone, taking care not to disturb the mantle of cement on the bone surface. Excess cement will generally be removed from the bone within the shell.

Accordingly, the present invention has the advantage that it provides an even distribution of bone cement on the surface of the head of a bone. Furthermore, the invention results in an even penetration of cement into the cancellous bone around the femoral head therefore reducing the risk of cell necrosis. The present invention ensures that the cement is applied and pressurised to all required areas of the femoral head. The high viscosity cement is applied in a dough-like phase and therefore increases the time period over which the bone cement may be applied to the head of the bone and apply the implant. The amount of excess bone cement extruded will be minimised therefore reducing the risk of scratching. The instrument allows a consistent depth of cement to be applied to the head of the bone therefore minimising the risk of incomplete seating of the implant.

In another aspect, the invention provides apparatus for use in resurfacing of the head of a bone which provides the ball component of a ball and socket joint, which comprises an instrument as discussed above and a quantity of a bone cement. Preferably, the viscosity of the cement, after mixing and before application to the surface of the bone, is at least about $10^6$ cp. Preferably, the apparatus includes a resurfacing shell which has a polished external surface which can function as a bearing surface, and which defines an internal cavity in which the head of the bone can be received.

The size and shape of the internal cavity in the resurfacing shell will generally correspond approximately to the space which is defined by the rib (or ribs) as the shell is rotated on the head of a bone so that all, or at least most, of the internal surface of the resurfacing shell contacts the resulting cement mantle on the bone head when it is properly seated.

The instrument of the invention can be used with high viscosity bone cements which do not flow readily. Such bone cements have a dough like consistency and are substantially self-supporting so that a quantity of the cement does not flow significantly when left to stand for a period of about 10 minutes. This allows a cement to be manipulated when used in a surgical procedure, after it has been mixed. Such a cement can be applied to the head of bone manually, for example by finger packing or by use of a syringe system. The advantage of using a syringe system is that this provides a 'no touch' method of application of the bone cement. Generally, the viscosity of a high viscosity cement, before application to the surface of the bone, will be at least about $10^6$ cp, preferably at least about $1.5 H 10^6$ cp.

Preferably, the shell has a plurality of ribs on its internal surface which are distributed approximately equally around the axis of the shell. Ribs on the internal surface of the shell can help to stabilise the shell on the surface of the bone against wobbling motion as the shell is rotated on the bone. This can be important when the shell is not located securely on the bone, for example by means of the spike located in a recess in the bone, or when the shell is formed from a material which can flex under manually applied forces. It will often be preferred for the shell to have at least three ribs on its internal surface, more preferably at least four ribs. More ribs can be provided, for example at least six ribs. The number and size of the ribs should be such that there is sufficient space within the shell between the ribs for excess cement to accumulate.

Preferably, the angle between the rib (or at least one of the ribs, when there is more than one rib) at its end closest to the spike like projection and a radius extending from the axis of the hollow shell is at least about 10 degrees. Such an arrangement of the rib at its polar end can help the rib to displace excess cement from the region around the pole of the bone, into the regions of the shell surrounding the surface of the bone which face outwardly relative to the bone axis. This can help to reduce the risk of an undesirable accumulation of cement in the region of the bone close to its axis.

Preferably, the angle between the surface of the rib, at least in those portions of the rib which contact the cement in regions of the head of the bone which face generally away from the bone axis, where it contacts a layer of bone cement on the head of the bone when the instrument is in use, and a radius extending from the axis of the shell, is at least about 10 degrees, more preferably at least about 30 degrees, especially at least about 45 degrees, for example at least about 75 degrees. This arrangement can help to generate forces on the cement towards the bone axis, to facilitate penetration of bone cement into the porous structure of cancellous bone.

Preferably, the rib is capable of being compressed towards the internal surface of the shell by cement which it contacts when the shell is rotated around its axis on the head of the bone. Compression of the rib will depend on factors which include the viscosity of the bone cement, which should be taken into account when designing the instrument to ensure that the thickness of the mantle of bone cement is adequately controlled. The compression of the rib can involve the rib being bent relative to the internal surface of the shell. This can be appropriate when the rib is narrow (when viewed in cross-section along its length), for example in the manner of a fin. Such a rib can be arranged in the absence of a bending force so that it extends approximately perpendicularly from the internal surface of the shell. It can be preferred for some applications that the rib be arranged so that it extends inclined to the surface of the shell. Such inclination, whether as a result of a compressive force or without a force, can help to ensure that the angle between the surface of the rib where it contacts a layer of bone cement on the head of the bone when the instrument is in use, and a radius extending from the axis of the shell, is 10 degrees or more. The fin can be tapered so that it is narrower at its tip than at the root where it is connected to the body of the shell.

The rib can have a rounded cross-section when viewed along its length, at least over part of its length. For example, the ribs can be approximately hemispherical in cross-section.

The thickness of the layer of the bone cement that is provided on the surface of the head of the bone is determined by factors including the space between the surface of the head of the bone and the ribs when they are swept over the surface of the cement-covered head, and the compressibility of the rib (or ribs) which will be affected by the viscosity of the cement, as discussed above.

Preferably, the instrument is designed so that a mantle of cement is formed on the surface of the head of the bone which is at least about 0.5 mm thick, more preferably at least about 0.75 mm thick. Preferably, the instrument is designed so that the thickness of the mantle is not more than about 2.0 mm, more preferably not more than about 1.5 mm, especially not more than about 1.25 mm.

The rotation of a shell to apply pressure to the cement mantle can enable pressure to be applied to the mantle more uniformly than if the resurfacing head itself is relied on to apply the pressure, while being positioned on the head of the bone. This can enable penetration of the cement into the porous structure of the bone to be more uniform, including into surfaces of the bone which face generally radially outwardly relative to the polar axis of the head of the bone as well as into the surfaces around the pole. This can enable the interface between the bone and the resurfacing shell to withstand torsional forces more effectively. It can provide greater resistance to ingress of foreign particles at the interface between the head of the bone and the implant at its periphery can be negligible. It can also provide a more uniform distribution of bone cement around the head of the bone; in particular, the tendency for cement to collect at the pole can be reduced. This therefore reduces the risk of localised accumulation of bone cement which may lead to a higher than normal temperature as the cement cures, possibly leading to damage of the bone tissue in some circumstances.

The shell can be provided by a rigid material so that the shell is not deformed significantly when rotated about the polar axis of the head of the bone. The shell might be reinforced by one or more reinforcing webs, generally on its external surface. Preferred techniques for making the instrument of the invention include casting and moulding.

Suitable materials can include polymers and metals such as those which are commonly used in surgical instruments. Suitable polymers might include certain polypropylenes, polycarbonates, polyesters and polyamides. Suitable metals might include certain stainless steels.

The thickness of the wall of the shell will be selected to ensure that the shell has the structural properties which are required for it to perform satisfactorily. The thickness that is required will also depend on the material which is used, consistent with it having the required structural properties.

The shell may be formed from a flexible material such as a silicone rubber. It is an advantage of using a flexible material for the shell that it can be formed as a single component with ribs which can be compressed when the shell is rotated in use. The shell may be supported by a support structure, which might for example be located around the outside of the wall member. The shell might have one or more grooves formed in it in which the support structure can be received, to reinforce the shell against unwanted expansion. It can be particularly preferred to reinforce the shell at a point towards its open face. The support can be provided by a component which is less deformable than the material of the shell. An example of a suitable component might be for example a band with a ratchet closure (sometimes referred to as a "tie-wrap").

The material of the ribs should be selected so that the ribs are suitably stiff to be able to displace bone cement material as the instrument is rotated on the head of the bone. A suitable material will generally have a Shore hardness of not more than about 100, preferably not more than about 80, for example not more than about 70. A suitable material will generally have a Shore hardness of at least about 10, preferably at least about 15, more preferably at least about 25.

The shell can be reinforced by a support structure, for example in the form of a cover. A support structure can be provided by a cover of relatively rigid material (for example a rigid polymer such as a moulded polyolefin or polyester or polyamide or polycarbonate, or a metal). The use of a support structure can be preferred when the shell is formed from a deformable material, especially a material which has a low Shore hardness. The support can cover at least part of the external surface of the shell, or it can be embedded in the wall of the shell. Alternatively, the shell can be provided by a rigid polymer or a metal. In this embodiment, it will often be preferred that the rib be provided by a different material, especially a material with a Shore hardness within one or more of the limits referred to above.

Preferably, the surface of the inner wall of the shell is provided by a release material so that adhesive forces between bone cement materials and the inner wall of the shell are minimal. This allows the shell to be removed cleanly from the cement mantle on the head of the bone. Examples of suitable release materials for use with available bone cement materials will be known to the skilled reader. Silicone rubber based materials are suitable for many applications. The release material can be provided as a surface layer of coating on the inner wall of the shell. The wall of the shell can consist essentially of the release material.

Preferably, the instrument includes a stem hole occluder. A stem hole occluder can be positioned in a bore in the bone, to prevent passage of bone cement into the bore. A stem hole occluder can be provided as a component which is separate from the shell and which is fitting into a bore in the head of the bone before the head of the bone is located within the shell.

A stem hole occluder can be connected to the shell, at least during the period in which the shell is closed around the head of the bone, so that the occluder can be removed from within the bore in the bone at the same time as the shell is removed from around the bone.

The viscosity of a bone cement can be measured using a viscometer. An example of a suitable instrument is that available under the trade name Brookfield RVDV-III. The reactive bone cement components (generally a powder and a liquid) should be at 23EC before mixing, and should be thoroughly mixed (in line with manufacturers' instructions) before the viscosity measurements are taken.

Generally, the resurfacing shell which is fitted on to the head of the bone will define an internal cavity which is rotationally symmetrical so that the cross-sectional shape of the cavity on the plane containing the polar axis remains substantially unchanged around the shell. Generally the cavity will comprise a polar surface which is approximately planar, perpendicular to the polar axis, and a side wall which is inclined to the polar axis. Preferably, the included angle between the side wall and the polar axis at the edge of the side wall where it intersects the polar surface is at least about 5 degrees, for example about 10 degrees. The included angle will generally be less than about 20 degrees.

The head of the bone can be prepared using a reamer. A tool which can be used to prepare the head in this way is disclosed in International patent application no. GB03/04303.

The shell in the instrument of the invention will define a cavity which has a shape similar to the shape of the cavity in the resurfacing shell which is to be used, so that the shape of the cement mantle which is created on the head of the bone is similar to the cavity within the resurfacing shell. Generally, the cavity in the shell of the instrument will be slightly bigger than the cavity in the resurfacing shell. For example, the radius or depth of the cavity in the shell of the instrument might be bigger than the radius or depth of the cavity in the resurfacing shell by at least about 0.7 mm, preferably at least about 1.0 mm, more preferably at least about 1.5 mm. This can provide for a mantle around the head of the bone of a predetermined thickness.

Preferably, the shell of the invention includes at least one locator within it, which extends inwardly from the internal surface of the shell, to contact the bone and to locate the shell relative to the bone. The locator is intended to contact the surface of the resected bone so that the shell is located relative to the surface, along the axis of the bone or transversely relative to it, or preferably both. Preferably, the shell includes a plurality of locators. For example a plurality of locators can extend inwardly from the side wall of the shell to locate the shell transversely relative to the bone. Preferably, there are at least three such locators. They might be provided, for example, at or close to the upper edge or the lower edge or both of the side wall of the shell. One or more locators can also be provided to extend towards the upper surface of the bone, to locate the shell along the axis of the bone.

Preferably the or each locator has a small cross-section so as to minimise its interference with the flow of cement within the shell. For example, locators can have the configuration of small pins. The cross-sectional shape and size of the pins will depend on factors such as the size of the shell, the intended thickness of the cement mantle (and therefore the length of the pins), the material from which the pins are formed and so on. When the shell is provided by a rigid material which is not deformed significantly under pressure, such as a metal or a polymer, the pins can be formed with the shell, for example by a moulding or casting process. When the shell comprises a flexible wall member, and a supporting frame positioned outside the wall member, the pins can be formed with the supporting frame, so that they extend through holes formed in the wall member.

Preferably, the length of the or each locator is at least about 2 mm, more preferably at least about 3 mm, for example at least about 4 mm. Preferably, the length of the or each locator is not more than about 8 mm, more preferably not more than about 6 mm.

Optionally, the shell can have a suction port through which a suction pump can be connected to remove air and blood from the space within the shell. The suction port can communicate with the stem hole to remove fluids from that region.

Embodiments of the invention will now be described by way of example with reference to the accompanying drawings, in which.

Figure 1:
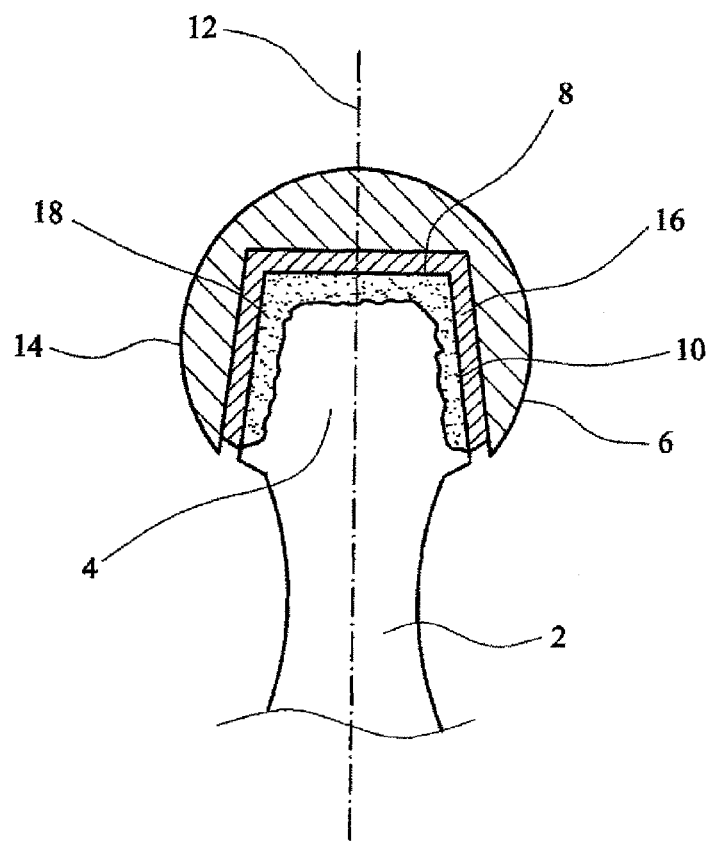
FIG. 1 is a cross-section through a femoral head which has a resurfacing shell fitted to it.

Referring to the drawings, FIG. 1 shows the neck 2 and head 4 of a femur to which a resurfacing shell 6 has been affixed using a high viscosity bone cement. It should be noted that the present invention can be used in relation to bones other than the femur, including for example the humerus.

The head 4 of the femur has been prepared to receive the resurfacing shell 6 by reaming it to form a generally planar surface 8 facing along the axis 12 of the femoral neck and head, and a side surface 10 which is inclined to the axis 12 so that the angle between the side surface and the axis is about 7 degrees.

The resurfacing shell 6 defines an internal cavity in which the head of the femur is fitted. The shape of the cavity corresponds to the shape of the reamed head but it is sized so that there is a gap between it and the surface of the bone which is about 1 mm thick. The resurfacing shell 6 has an external surface 14 which is polished as is known, to provide a bearing surface which can articulate with a corresponding bearing surface of an acetabular component.

A mantle of a high viscosity bone cement 16 such as that sold by DePuy CMW under the trade mark SmartSet GHV is provided between the surface of the bone and the internal surface of the cavity in the resurfacing shell 6. The viscosity of the cement is such that the cement is self supporting when applied to the prepared head of the bone, so that it does not tend to fall off the surface after application and before the resurfacing shell is applied. Techniques for applying such high viscosity cements are known, often involving manual application.

For secure fixation of the resurfacing shell 6 on to the prepared bone, it is preferred that the high viscosity bone cement should penetrate the porous bone tissue of the head as shown at 18 in FIG. 1. This can be achieved be applying pressure to the bone cement before it cures. It is preferred that the bone cement should penetrate the surface of the head in the side surface regions as well as the top surface region.

It is also desirable that the thickness of mantle of cement on the surface of the bone should be approximately uniform, in particular so that the amount of the cement on the surface surrounding the axis of the bone is not significantly greater than a predetermined thickness (generally about 1 mm). It is also desirable that the amount of cement on the side surface of the prepared bone should not be significantly less than a predetermined thickness (generally about 1 mm).

Figures 2A, 2B, 2C:
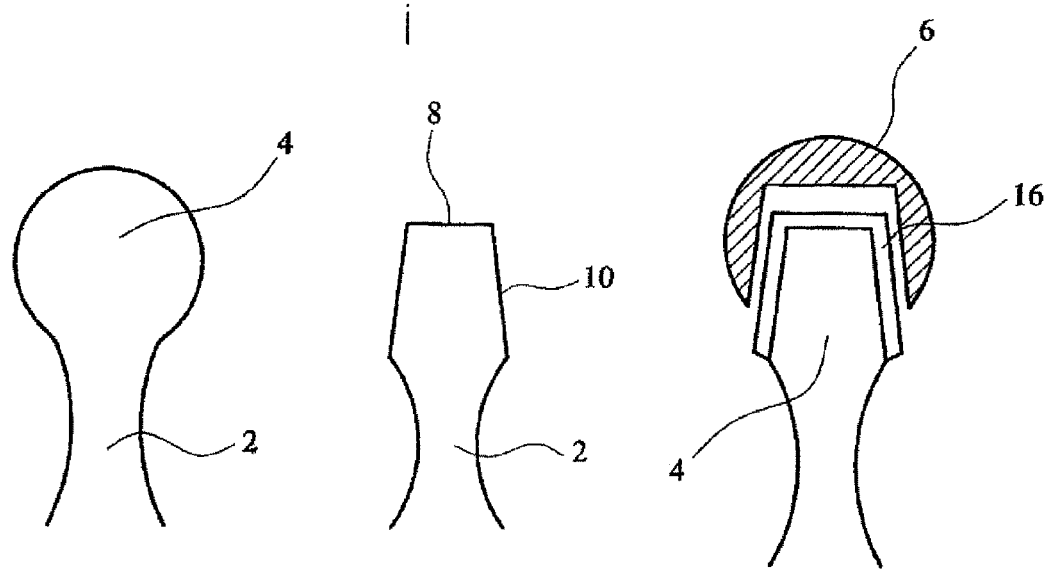
FIG. 2 shows steps in a method of fitting a resurfacing shell to a femoral head.

FIG. 2a shows the head 4 and neck 2 region of a femur before bone tissue is resected. FIG. 2b shows the head after it has been resected, for example using a reamer of the type disclosed in International patent application no. GB03/04303, so that it has a generally planar top surface 8 and a side surface 10.

FIG. 2c shows the head with a mantle 18 of high viscosity bone cement such as that sold by DePuy CMW under the trade mark SmartSet GHV formed around it, prior to a resurfacing shell 6 being fitted over the head. The bone cement is applied to the head of the bone manually by finger packing or by use of a syringe system. The bone cement has a dough like consistency and is self supporting. The viscosity of the bone cement can be measured using a viscometer. An example of a suitable instrument is that available under the trade name Brookfield RVDV-III. The temperature of the reactive bone cement components is 23 EC prior to mixing. The bone cement components are thoroughly mixed before the measurements are taken. The viscosity of the bone cement is at least $10^6$ cp.

Figure 3:
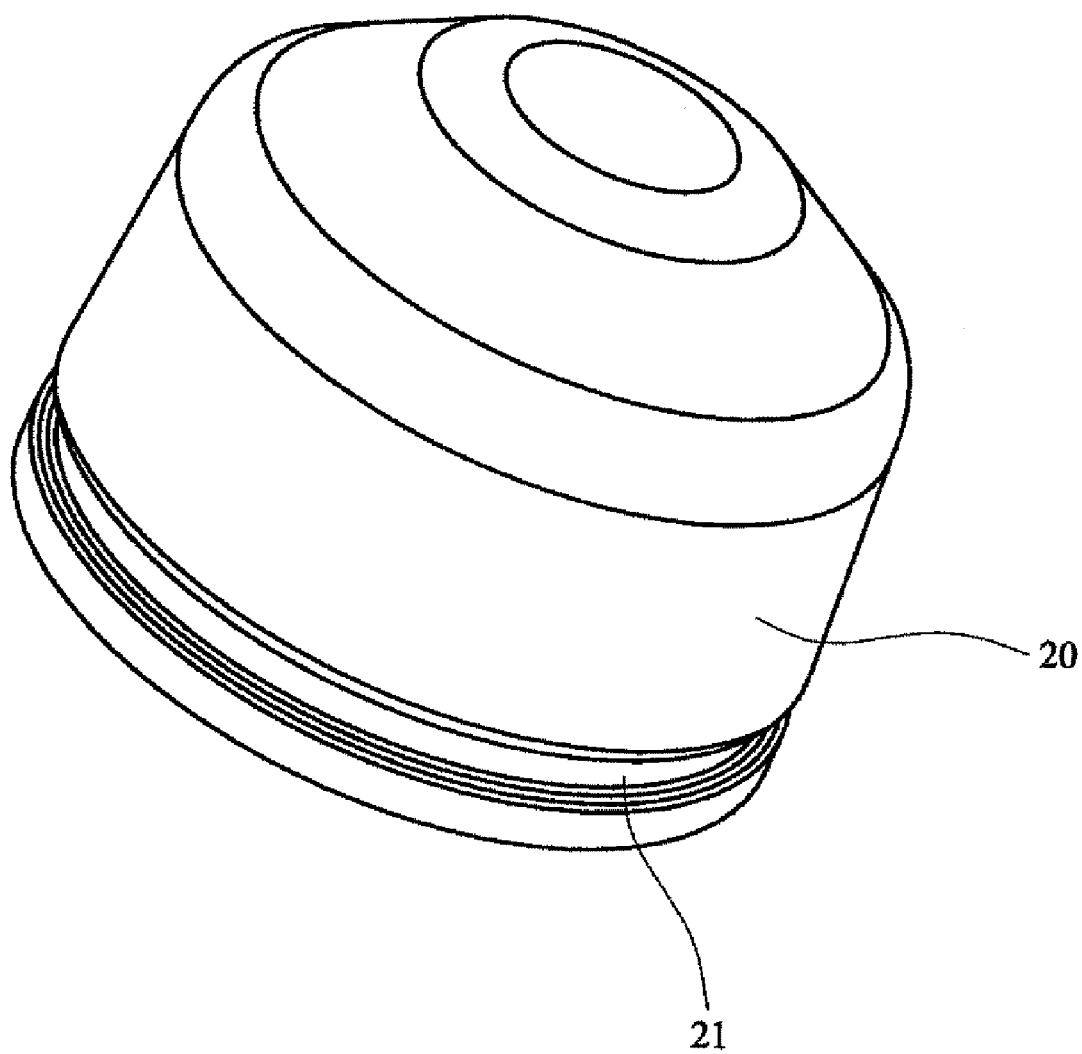
FIG. 3 shows the external side view of the instrument of the present invention.

FIG. 3 shows the external side view of the instrument of the present invention comprising a hollow shell 20 being rotationally symmetrical. The instrument of the present invention is formed as a single component from silicon rubber with ribs which can be compressed when the shell is rotated in use. The shell 20 has a groove 21 formed in it towards its open face, which can receive a support band, for example a band with a ratchet closure (sometimes referred to as a "tie-wrap").

Figure 4A:
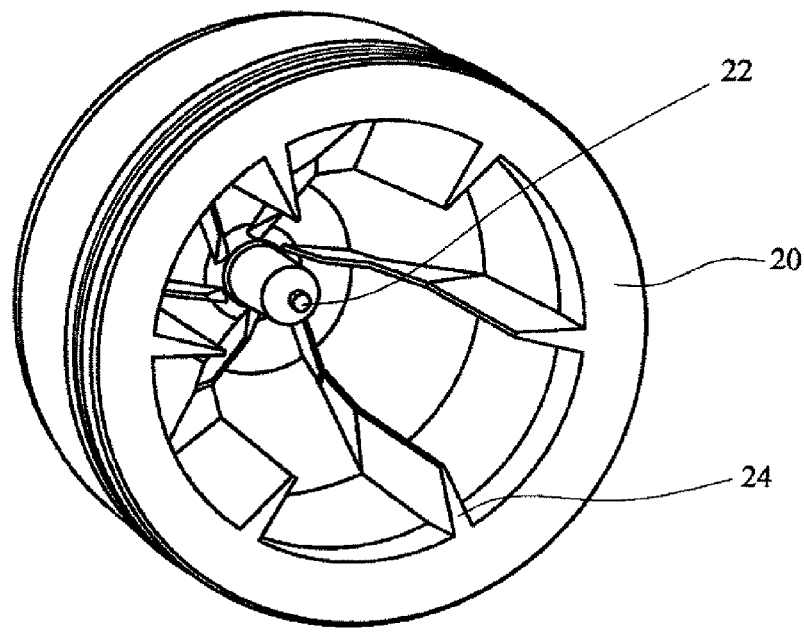
FIG. 4a shows the internal view of the instrument of the present invention at an angle to the rotational axis of the shell.
Figure 4B:
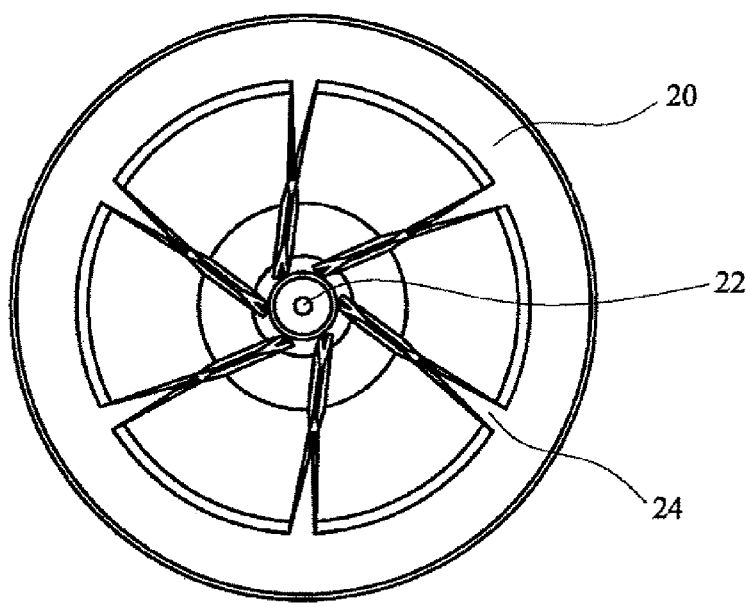
FIG. 4b shows the internal view of the instrument of the present invention along the rotational axis of the shell.

FIGS. 4a and 4b show the internal view of the instrument of the present invention comprising a hollow shell 20 being rotationally symmetrical and having a spike like projection 22 extending axially from the internal surface of the shell and having six ribs or fins 24 located on the internal surface of the shell 20 extending from the spike like projection 22 towards the open face of the shell 20. The instrument is made as a single component from silicon rubber with ribs which can be compressed when the shell is rotated in use. The hollow shell has a thickness of 10 mm.

The spike like projection 22 defines the depth of the cavity between the surface of the bone and the internal surface of the shell, at and around the bone axis. The spike like projection 22 ensures that bone cement is adequately displaced from the region of the shell around the axis. The ribs 24 are distributed approximately equally around the axis of the shell 20 and extend approximately perpendicularly from the internal surface of the shell 20. The angle between the rib 24 at its end closest to the spike like projection 22 and a radius extending from the axis of the hollow shell 20 is 10 degrees.

The instrument is fitted on the head of a bone which has been pre-coated with a high viscosity bone cement such as that sold by DePuy CMW under the trade mark SmartSet GHV. The high viscosity bone cement may be applied by finger packing or by using a syringe system. The silicon rubber ribs 24 are compressed towards the internal surface of the silicon rubber shell when the instrument is rotated about its axis on the head of the bone. The arrangement of the ribs 24 ensures that the ribs 24 contact the bone cement on the head of the bone in a sweeping action.

The bone cement which is caught by the rib 24 as it sweeps over the head of the bone accumulates in the cavity within the shell adjacent to the rib 24. The action of the rib 24 as it is swept over the surface of the bone cement can help to cause the cement to penetrate into the porous structure of cancellous bone.

The ribs 24 bend relative to the internal surface of the shell 20 during rotation of the instrument. The rotation of the instrument and the sweeping of the ribs 24 along the surface of the bone cement ensures that the cement is applied and pressurised to all areas of the head of the bone.

The thickness of the bone cement mantle formed on the head of the bone is determined by the space between the surface of the head of the bone and the ribs 24 when they are swept along the surface of the cement covered head, the compressibility of the ribs 24 and the viscosity of the bone cement. The cement mantle provided by rotation of the instrument has a thickness of 1 mm. The resulting smooth cement mantle on the head of the bone contacts the internal surface of the resurfacing shell 6 when it is properly seated.

As the shell 20 and the ribs 24 are made from silicon rubber the adhesive forces between a high viscosity bone cement and the inner wall of the shell 20 are minimal. The shell 20 is able to be removed cleanly from the cement mantle on the head of a bone after the bone cement on the head of the bone has been distributed so as to provide a smooth cement mantle the instrument is removed from the bone. The excess bone cement in the spaces between the ribs is removed from the bone with the shell.

The invention claimed is:

1. An instrument for controlling the distribution of bone cement on the surface of the head of a bone to prepare the bone to receive a re-surfacing prosthesis, comprising:
   a hollow shell having an open face and an internal surface that defines a cavity, the cavity sized to permit the head of the bone to be disposed therein and define a space around the head, the hollow shell being rotationally symmetrical and having a projection extending axially from the internal surface; and
   at least one rib extending radially inwardly from the internal surface of the shell, and wherein the at least one rib has a distal end and is configured to be flexible such that, when the shell is rotated with respect to the bone and the distal end contacts the bone cement, the at least one rib is compressed toward the internal surface of the shell.

2. The instrument of claim 1, wherein the at least one rib is a plurality of ribs extending from the internal surface at locations distributed approximately equally around the axis of the shell.

3. The instrument of claim 2, wherein the plurality of ribs comprises at least four ribs.

4. The instrument of claim 1, wherein the angle between the rib at its end closest to the projection and a radius extending from the axis of the hollow shell is at least about 10 degrees.

5. The instrument of claim 1, wherein the angle between the surface of the rib where the distal end of the rib contacts a layer of bone cement on the head of the bone when the instrument is in use, and a radius extending from the axis of the shell, is at least about 10 degrees.

6. The instrument of claim 5, wherein the angle is at least about 45 degrees.

7. The instrument of claim 1, wherein the rib has a rounded cross-section when viewed along its length.

8. The instrument of claim 1, wherein the shell is formed from a rigid material which resists compression when the shell is gripped by the user.

9. The instrument of claim 1, wherein the rib is formed from the same material as the material of the shell.

10. The instrument of claim 1, wherein the shell is formed from a silicone rubber.

11. The instrument of claim 1, wherein the at least one rib extends from the internal surface at least at a location near the projection of the shell.

12. The instrument of claim 1, wherein the at least one rib extends from the face of the shell.

13. The instrument of claim 1, wherein the at least one rib has a length measured from the inner surface of the shell to the distal end of the rib, and the length increases from a point near the projection to a point near the face of the shell.

14. An apparatus for use in resurfacing of the head of a bone which provides the ball component of a ball and socket joint, comprising
   a hollow shell having an open face and an internal surface that defines a cavity, the cavity sized to permit the head of the bone to be disposed therein and define a space around the head, the hollow shell being rotationally symmetrical and having a projection extending axially from the internal surface;
   at least one rib extending radially inwardly from the internal surface of the shell, the at least one rib having a distal end and being configured to be flexible such that, when the shell is rotated with respect to the bone and the distal end of the at least one rib contacts the bone cement, the at least one rib is compressed toward the internal surface of the shell; and
   a quantity of a bone cement.

15. The apparatus of claim 14, wherein the viscosity of the cement, before application to the surface of the bone, is at least about 106 cp.

16. The apparatus of claim 14, further comprising a resurfacing shell which has a polished external surface which can function as a bearing surface, and which defines an internal cavity wherein the head of the bone can be received.

17. The instrument of claim 14, wherein the at least one rib extends from the internal surface at least at a location near the projection of the shell.

18. The instrument of claim 14, wherein the at least one rib extends from the face of the shell.

19. The instrument of claim 14, wherein the at least one rib has a length measured from the inner surface of the shell to the distal end of the rib, and the length increases from a point near the projection to a point near the face of the shell.

20. An instrument for controlling the distribution of bone cement on the surface of the head of a bone to prepare the bone to receive a re-surfacing prosthesis, comprising:
   a hollow shell having an open face and an internal surface that defines a cavity, the cavity sized to permit the head of the bone to be disposed therein and define a space around the head, the hollow shell being rotationally symmetrical and having a projection extending axially from the internal surface; and
   at least one rib extending radially inwardly from the internal surface of the shell, and wherein the at least one rib has a distal end and the at least one rib is configured such that the distal end bends relative to the internal surface of the shell when compressed.

21. The instrument of claim 20, the at least one rib configured to be flexible such that, when the shell is rotated with respect to the bone and the distal end of the at least one rib contacts the bone cement, the at least one rib is compressed toward the internal surface of the shell.

22. The instrument of claim 20, wherein the at least one rib extends from the internal surface at least at a location near the projection of the shell.

23. The instrument of claim 20, wherein the at least one rib extends from the face of the shell.

24. The instrument of claim 20, wherein the at least one rib has a length measured from the inner surface of the shell to the distal end of the rib, and the length increases from a point near the projection to a point near the face of the shell.

* * * * *